US006239056B1

(12) United States Patent
Gajda et al.

(10) Patent No.: US 6,239,056 B1
(45) Date of Patent: May 29, 2001

(54) SELECTIVE AROMATICS DISPROPORTIONATION PROCESS

(75) Inventors: Gregory J. Gajda, Mount Prospect; Edwin P. Boldingh, Arlington Heights; Jennifer S. Holmgren, Bloomingdale, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/467,852

(22) Filed: Dec. 20, 1999

Related U.S. Application Data

(62) Division of application No. 09/213,959, filed on Dec. 17, 1998, now Pat. No. 6,063,977.

(51) Int. Cl.[7] .................................................. B01J 29/06
(52) U.S. Cl. .............................. 502/64; 502/60; 502/71; 502/77
(58) Field of Search ................................ 502/60, 64, 71, 502/77

(56) References Cited

U.S. PATENT DOCUMENTS

| 4,011,276 | 3/1977 | Chu | 260/672 T |
|---|---|---|---|
| 4,016,219 | 4/1977 | Kaeding | 260/672 T |
| 4,097,543 | 6/1978 | Haag et al. | 260/672 T |
| 4,182,923 | 1/1980 | Chu | 585/475 |
| 4,605,637 | * 8/1986 | Chang et al. | 502/64 |
| 4,629,717 | 12/1986 | Chao | 502/208 |
| 4,975,180 | * 12/1990 | Eberly | 208/114 |
| 5,169,812 | 12/1992 | Kocal et al. | 502/61 |
| 5,888,921 | * 3/1999 | Tsang et al. | 502/64 |
| 5,905,051 | * 5/1999 | Wu et al. | 502/60 |
| 5,990,032 | * 11/1999 | Wu et al. | 502/71 |
| 6,080,303 | * 6/2000 | Cao et al. | 208/120.01 |

* cited by examiner

*Primary Examiner*—Tom Dunn
(74) *Attorney, Agent, or Firm*—John G. Tolomei; John F. Spears, Jr.

(57) ABSTRACT

An improved catalyst and process are disclosed for the selective disproportionation of toluene. The process uses a zeolitic catalyst which is oil-dropped in an aluminum phosphate binder and has an X-ray diffraction pattern showing characteristic intensities at specified Bragg angles. Optionally, the catalyst is selectively precoked prior to toluene disproportionation. The catalyst and process provide improved selectivity for the production of paraxylene.

9 Claims, 2 Drawing Sheets

SELECTIVE AROMATICS DISPROPORTIONATION PROCESS

CROSS REFERENCE TO RELATED APPLICATION

This application is a division of prior application Ser. No. 09/213,959, filed Dec. 17, 1998, now U.S. Pat. No. 6,063,977 the contents of which are incorporated herein by reference thereto.

BACKGROUND OF THE INVENTION

This invention relates to processes for the conversion of aromatic hydrocarbons, and is more specifically an improved process for disproportionation and transalkylation of aromatic hydrocarbons to obtain xylenes.

The xylene isomers are produced in large volumes from petroleum as feedstocks for a variety of important industrial chemicals. The most important of the xylene isomers is paraxylene, the principal feedstock for polyester which continues to enjoy a high growth rate from large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

A current objective of many aromatics complexes is to increase the yield of xylenes and to deemphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics along with toluene have been commercialized to obtain high xylene yields.

U.S. Pat. No. 4,016,219 (Kaeding) discloses a process for toluene disproportionation using a catalyst comprising a zeolite which has been modified by the addition of phosphorus in an amount of at least 0.5 mass-%. The crystals of the zeolite are contacted with a phosphorus compound to effect reaction of the zeolite and phosphorus compound. The modified zeolite then may be incorporated into indicated matrix materials.

U.S. Pat. No. 4,097,543 (Haag et al) teaches toluene disproportionation for the selective production of paraxylene using a zeolite which has undergone controlled precoking. The zeolite may be ion-exchanged with a variety of elements from Group IB to VIII, and composited with a variety of clays and other porous matrix materials.

U.S. Pat. No. 4,629,717 (Chao) discloses a phosphorus-modified alumina hydrogel formed by gelation of a homogeneous hydrosol. The composite has a relatively high surface area of 140–450 $m^2/g$ and high activity and selectivity in 1-heptene conversion tests.

U.S. Pat. No. 5,169,812 (Kocal et al) teaches a catalyst for aromatization of light hydrocarbons comprising a zeolite, preferably ZSM-5, a gallium component and an aluminum phosphate binder. The composite is treated with a weakly acidic solution, dried and calcined to increase its tolerance to hydrogen at high temperatures.

U.S. Pat. No. 4,011,276 (Chu) describes a toluene disproportionation process which employs a catalyst comprising n aluminosilicate zeolite, such as a ZSM-5 zeolite, which has been modified by the addition of phosphorous oxide and magnesium oxide to the zeolite.

U.S. Pat. No. 4,182,923 (Chu) describes a process for toluene disproportionation with high conversion of the toluene to benzene and paraxylene by use of an aluminosilicate zeolite of silica to alumina ratio above 12 and which has been modified by treatment with ammonium hydrogen phosphate to deposit phosphorous.

Workers in the field of aromatics disproportionation continue to seek processes and catalysts having exceptionally high selectivity for paraxylene from toluene combined with favorable activity and stability.

SUMMARY OF THE INVENTION

It is an object of the present invention to provide an improved process for the disproportionation of aromatic hydrocarbons to yield desirable alkylaromatic isomers. A specific objective is to obtain a high yield of paraxylene by disproportionation of toluene.

This invention is based on the discovery that high activity with potential for selectivity to paraxylene is obtained by disproportionation of toluene using a catalyst, having a particular X-ray diffraction pattern, comprising a zeolite oil-dropped with an aluminum phosphate binder.

The present invention therefore is directed to an oil-dropped spherical catalyst comprising a zeolitic aluminosilicate having a pore diameter of from about 5 to 8 A and an aluminum phosphate binder. The catalyst has an X-ray powder diffraction pattern such that the ratio of peak intensities at respective two-Θ Bragg angle values of 48.5:46.5 is at least about 1.1, and optimally the ratio of peak intensities at respective two-Θ Bragg angle values of 48.5:47.5 is at least about 1.0. The preferred catalyst of the present invention comprises a zeolitic aluminosilicate preferably selected from MFI, MEL and MTW, and most preferably comprises MFI. In one embodiment, the catalyst has a particle size of no more than about 1 mm.

The invention also comprises a process for the disproportionation of a toluene feedstock using the present catalyst to obtain a product comprising paraxylene. Preferably the product contains paraxylene in excess of its equilibrium concentration at disproportionation conditions. The catalyst preferably is subjected to a precoking step prior to its use for disproportionation/transalkylation in order to deposit a controlled concentration of carbon on the catalyst and increase its selectivity to paraxylene in the product. A process combination optionally comprises a xylene-separation zone using adsorptive separation.

These as well as other objects and embodiments will become apparent from the detailed description of the invention.

DESCRIPTION OF THE PREFERRED EMBODIMENTS

Figure 1:
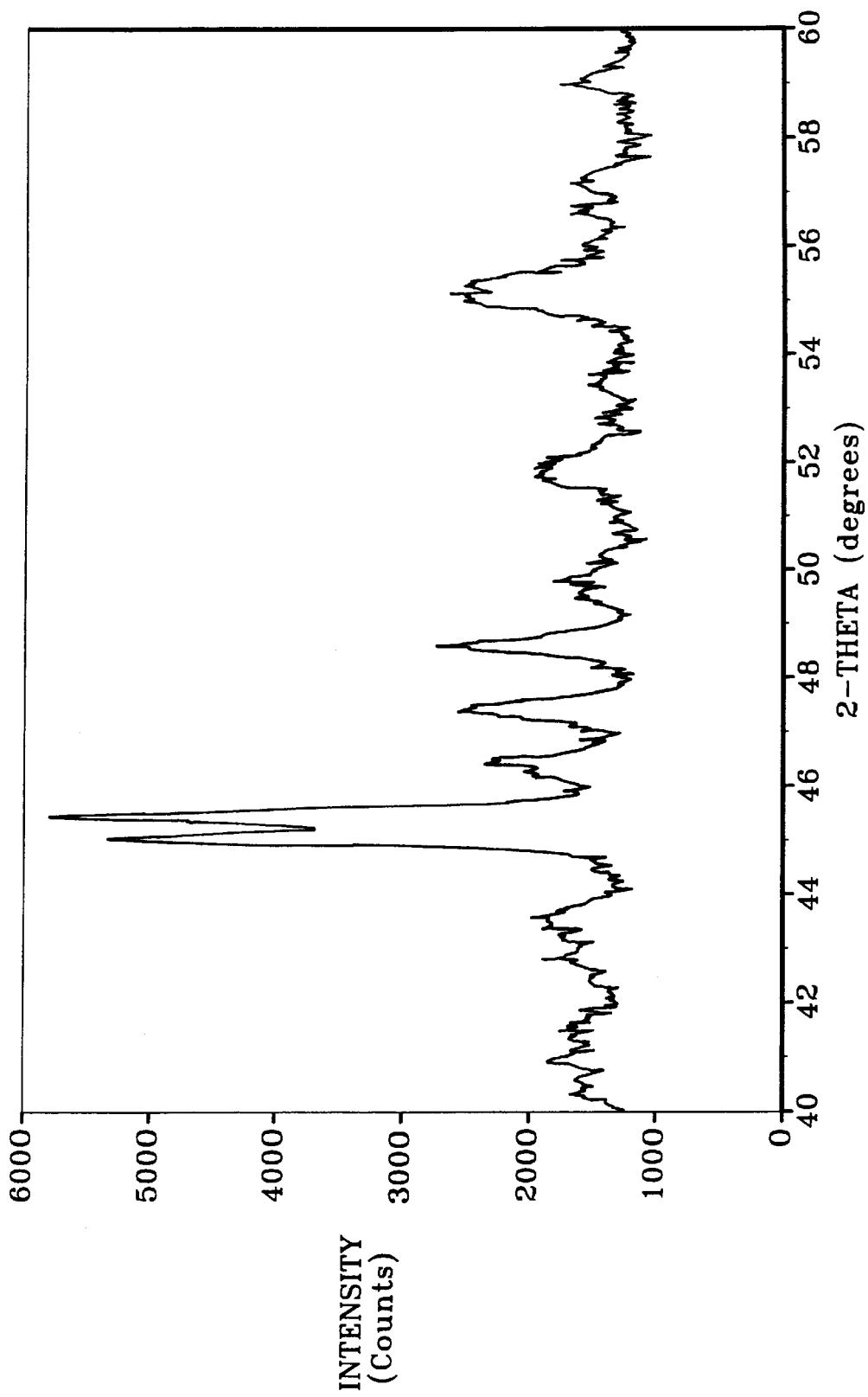
FIG. 1 shows an X-ray diffraction pattern for a catalyst of the invention.
Figure 2:
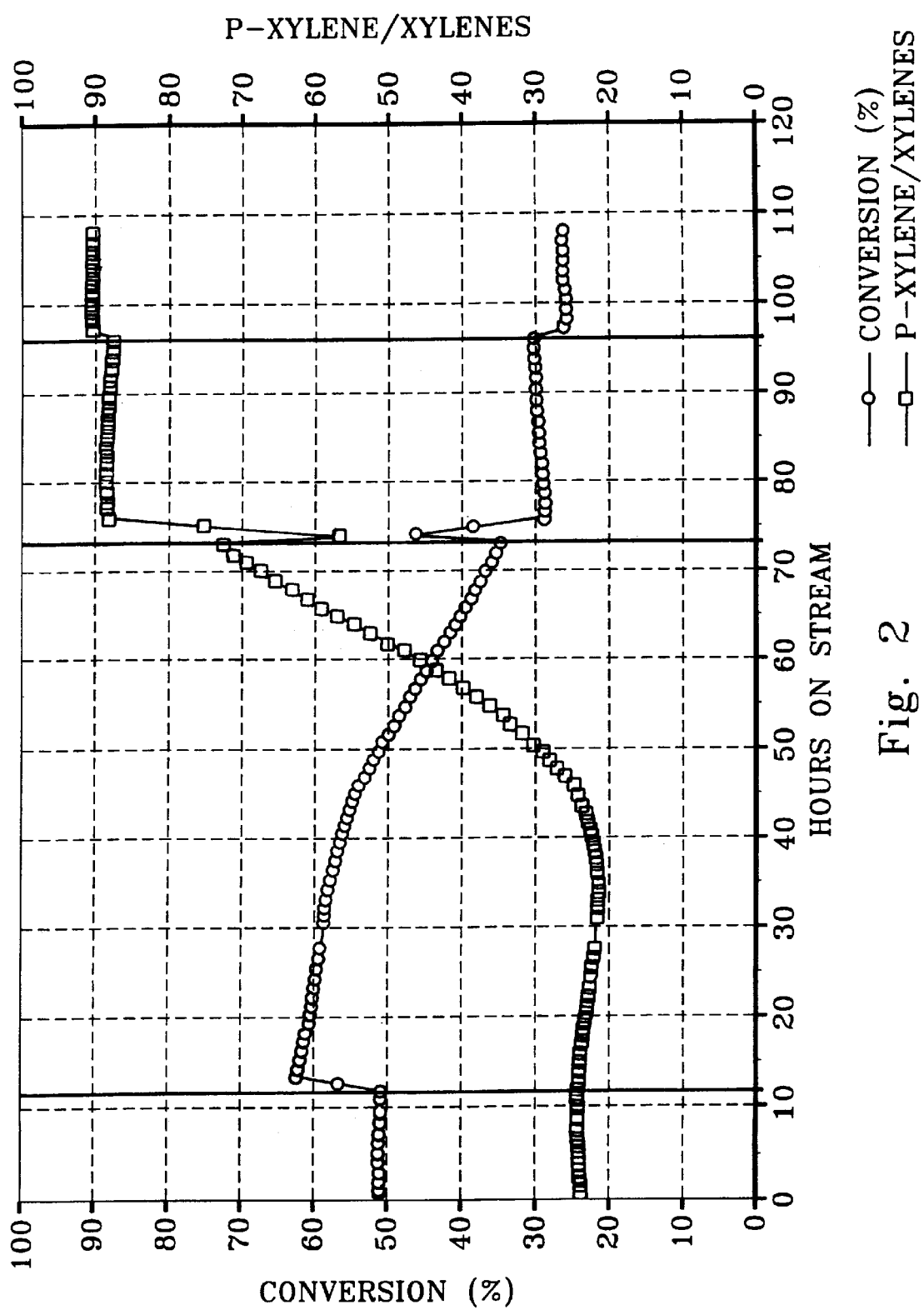
FIG. 2 shows conversion and selectivity in a pilot-plant test of toluene disproportionation.

An embodiment of the present invention therefore is directed to the disproportionation of a toluene feedstock to obtain a product comprising paraxylene using an oil-dropped spherical catalyst comprising a zeolitic alumino-silicate having a pore diameter of from about 5 to 8 Å and an aluminum phosphate binder. The catalyst is characterized by a specific X-ray powder diffraction pattern such that the ratio of peak intensities at respective two-Θ Bragg angle values of 48.5:46.5 is at least about 1.1; optimally, moreover, the ratio of peak intensities at respective two-Θ Bragg angle values of 48.5:47.5 is at least about 1.0. The paraxylene content of the product preferably is in excess of its equilibrium concentration at disproportionation conditions. Other embodiments of the invention encompass but are not limited to parameters such as incremental and alternative feedstocks, catalyst composition, catalyst conditioning for paraxylene selectivity and operating conditions.

In a broad embodiment, the feedstock to the subject process comprises substantially pure aromatic hydrocarbons derived from one or more sources. Aromatics may be produced synthetically, for example, from naphtha by catalytic reforming or by pyrolysis followed by hydrotreating to yield an aromatics-rich product. The aromatics feedstock may be derived from such product with suitable purity by extraction of aromatic hydrocarbons from a mixture of aromatic and nonaromatic hydrocarbons and fractionation of the extract. Large quantities of aromatic hydrocarbons are recovered commercially in this manner. For instance, aromatics may be recovered from a reformate through the use of a selective solvent, such as one of the sulfolane type, in a liquid-liquid extraction zone. When the severity of reforming or pyrolysis is sufficiently high, extraction may be unnecessary and fractionation may be sufficient to prepare the feedstock which should contain no more than about 10 mass-% and preferably less than about 1 mass-% nonaromatics. The recovered aromatics may then be separated into streams having the desired carbon number range by fractionation. The aromatic hydrocarbons may comprise one or more of toluene, xylene isomers, ethylbenzene, or $C_9$ and heavier aromatics. A preferred toluene feedstock prepared in this manner usually is fractionated to separate benzene and $C_8$ aromatics, and the degree of fractionation may be adjusted in accordance with economic factors of the disproportionation process.

The toluene feedstock, usually in admixture with toluene recycled from the products of the disproportionation reaction, is preferably admixed with free hydrogen to effect a combined feed to a disproportionation zone. If present, the hydrogen need not exceed a 20:1 molar ratio to feedstock hydrocarbons to effect satisfactory stability in the disproportionation reaction, and preferably is in the range of from about 0.5 to 10 molar ratio. The hydrogen may contain hydrocarbons, such as methane and ethane, and inerts such as nitrogen, but preferably is in a concentration of at least about 90 mole-% to avoid large hydrogen losses and unfavorable process economics. The disproportionation reaction yields a paraxylene-containing product which usually also comprises benzene, other $C_8$ aromatics, and smaller amounts of $C_9$+ aromatics.

The combined feed to the disproportionation zone usually is first heated by indirect heat exchange against the effluent of the reaction zone and is then further heated in a fired heater. The resulting vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both product and unconverted feed hydrocarbons. This effluent is normally cooled by indirect heat exchange against the stream entering the reaction zone and then further cooled through the use of air or cooling water. The temperature of the effluent stream generally is lowered by heat exchange sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all $C_5$ and lighter hydrocarbons present in the effluent are concentrated into an overhead stream and removed from the process. An aromatics-rich stream which is referred to herein as the disproportionation effluent stream is recovered as net stripper bottoms.

The catalyst preferably is subjected to precoking as described hereinbelow to increase the proportion of paraxylene in the $C_8$ aromatics product above equilibrium levels at disproportionation conditions.

Conditions employed in the disproportionation zone of the subject process normally include a temperature of from about 200° to 600° C., and preferably from about 350° to 575° C. The temperature required to maintain the desired degree of conversion will increase as the catalyst gradually loses activity during processing. Normal end-of-run temperatures may therefore exceed start-of-run temperatures by 65° C. or more. In the transalkylation embodiment wherein toluene and $C_9$ aromatics are present in the combined feed, reaction temperatures generally are somewhat lower within the range of about 200° to 525° C.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of paraxylene at the expense of conversion. Weight hourly space velocities generally are the range of from about 0.2 to 10 $hr^{-1}$.

It is within the scope of the invention that the combined feed includes a heavy-aromatics stream comprising $C_9$ aromatics as a component of the combined feed to the present process. Transalkylation of toluene and $C_9$ aromatics is effected thereby within the disproportionation conditions described hereinabove The heavy-aromatics stream may be derived from the same or different known refinery and petrochemical processes as the toluene feedstock and/or may be recycled from the separation of the product from disproportionation/transalkylation. Benzene also may be present in the combined feed to disproportionation/transalkylation. However, it is preferred that the feedstock consists essentially of toluene in order to effect a high degree of paraxylene selectivity as described hereinbelow.

The disproportionation effluent stream is separated into a light recycle stream, a paraxylene-containing mixed-$C_8$- aromatics product and a heavy-aromatics stream. The paraxylene-containing product may be sent to a xylene separation zone for recovery of pure paraxylene; optionally, other xylenes and ethylbenzene also may be recovered as pure products. The paraxylene-containing stream preferably contains paraxylene in proportion to total xylenes in excess of its equilibrium concentration at disproportionation conditions, more preferably at least about 80 mass-% paraxylene, and most preferably at least about 85 mass-% paraxylene. The light recycle stream may be diverted to other uses such as to benzene and toluene recovery, but optionally a portion is recycled to the disproportionation zone since it contains not only benzene and toluene but also amounts of nonaromatics which would remain with the benzene and reduce its commercial value. The heavy recycle stream contains substantially all of the $C_9$ and heavier aromatics and may be either withdrawn as a product of the process or partially or totally recycled to the reaction if transalkylation is an objective of the process.

The xylene-separation zone may utilize one or more different separation techniques such as fractionation, crystallization or selective adsorption to recover pure paraxylene from the paraxylene-containing stream in the xylene-separation zone. Conventional crystallization is disclosed in U.S. Pat. No. 3,177,255, U.S. Pat. No. 3,467,724 and U.S. Pat. No. 3,662,013. Various other crystallization alternatives are discussed in U.S. Pat. No. 5,329,061, incorporated by reference. In an embodiment in which the paraxylene-containing product has a paraxylene content substantially in excess of the equilibrium concentration, recovery of pure paraxylene may be effected using only a single stage of crystallization corresponding to the higher-temperature purification stage of conventional crystallization.

An alternative separation zone comprises a bed of molecular sieves operated in accordance with the teaching of U.S. Pat. No. 3,201,491 to simulate the use of a continuously moving bed of molecular sieves. Subsequent improvements to the process are described in U.S. Pat. No. 3,696,107 and U.S. Pat. No. 3,626,020. Details on the operation of the xylene-separation zone may also be obtained from U.S. Pat. No. 4,039,599 and U.S. Pat. No. 4,184,943. The simulated concurrent adsorptive separation process of U.S. Pat. No. 4,402,832 may be employed. The extract and raffinate streams may be handled as described in these references or as described in U.S. Pat. No. 4,381,419.

The skilled routineer will recognize variations in the process combination described above which are within the scope of the invention. For example, benzene as well as toluene may be charged to the disproportionation zone as a supplementary feedstock. The xylene-separation zone may use one or more of several known separation techniques such as adsorption, crystallization and fractionation. Orthoxylene and/or metaxylene may be recovered by one or more of such techniques as pure products from the xylene-separation zone.

The catalyst of the present invention comprises a molecular sieve and a refractory inorganic oxide. The preferred molecular sieves are zeolitic aluminosilicates which may be any of those which have a $Si:Al_2$ ratio greater than about 10, preferably greater than 20, and a pore diameter of about 5 to 8 Angstroms (Å). Specific examples of zeolites which can be used are the MFI, MEL, EUO, FER, MFS, MTT, MTW, TON, MOR and FAU types of zeolites. Pentasil zeolites MFI, MEL, MTW and TON are preferred, and MFI-type zeolites, often designated ZSM-5, are especially preferred.

The preparation of the preferred MFI-type zeolites is well known in the art. The zeolites generally are prepared by crystallizing a mixture containing an alumina source, a silica source, an alkali metal source, water and an alkyl ammonium compound or its precursor. The amount of zeolite present in the catalyst can vary considerably but usually is present in an amount from about 30 to 90 mass percent and preferably from about 50 to 80 mass percent of the catalyst.

Preferably the zeolite has an enhanced surface silicon content, i.e., the proportion of silicon at the surface of the zeolite is greater than the proportion in the bulk of the zeolite. The "surface" is defined for purposes of the present invention as a layer at the external surface of the zeolite which is less than about 100 angstroms in depth, and usually about 10 angstroms or less in depth. Optimally the silicon/aluminum ratio, expressed as $Si/Al_2$, is increased by about 5 or more at the surface of the zeolite relative to the ratio in the bulk of the zeolite. Elemental surface analysis to assess component ratios is effected by any suitable method as taught in the art, e.g., XPS, Auger spectroscopy or SIMS. XPS, or x-ray photoelectron spectroscopy, is particularly effective in determining surface ratios of framework components.

An enhanced surface silicon content is effected by treating the zeolite with a dilute acid solution or an aqueous solution of a weakly acidic ammonium salt, either as the bound zeolite or preferably before being composited with a binder. Preferred dilute acids for treating the unbound zeolite include hydrochloric, acetic, nitric, phosphoric and especially sulfuric acids. Ammonium salts which can be used include ammonium chloride, ammonium acetate, and especially ammonium nitrate for treating the bound zeolite. The treating solution is contacted with dried catalyst particles at a temperature of from about 50° to 100° C. for a period of from about 1 to 48 hours, and the particles then are separated, dried, and calcined at a temperature of from about 500° to 700° C. for a period of from about 1 to 15 hours.

A refractory binder or matrix is utilized to facilitate fabrication of the disproportionation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, zinc oxide and silica. Alumina and/or silica are preferred binders.

A preferred binder or matrix component is a phosphorus-containing alumina (hereinafter referred to as aluminum phosphate) component. The phosphorus may be composited with the alumina in any acceptable manner known in the art. The zeolite and aluminum phosphate binder are mixed and formed into particles by means well known in the art such as gellation, pilling, nodulizing, marumerizing, spray drying, extrusion or any combination of these techniques. A preferred method of preparing the zeolitelaluminum phosphate support involves adding the zeolite either to an alumina sol or a phosphorus compound, forming a mixture of the alumina sol/zeolite/phosphorus compound into particles by employing an oil-drop method as described hereinbelow and calcining the spherical particles.

The preferred oil-drop method of preparing the aluminum phosphate is described in U.S. Pat. No. 4,629,717 which is incorporated by reference. The technique described in the '717 patent involves the gellation of a hydrosol of alumina which contains a phosphorus compound using the well-known oil-drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to 1.5:1 mass ratio. A phosphorus compound is now added to the sol. Preferred phosphorus compounds are phosphoric acid, phosphorous acid and ammonium phosphate. The relative amount of phosphorus and aluminum expressed in molar ratios ranges from about 10:1 to 1:100, respectively, on an elemental basis. The zeolite is added to the aluminum phosphate hydrosol and the mixture is gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The combined mixture preferably is dispersed into the oil bath in the form of droplets from a nozzle, orifice or rotating disk. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours The amount of phosphorus-containing alumina component present (as the oxide) in the catalyst can range from about 10 to 70 mass percent and preferably from about 20 to 50 mass percent. The aluminum phosphate binder/matrix optionally may contain lesser proportions of other inorganic oxides including, but not limited to, magnesia, beryllia, boria, silica, germania, tin oxide, zinc oxide, titania, zirconia, vanadia, iron oxide, chromia, cobalt oxide and the like which can be added to the hydrosol prior to dropping.

The aluminum-phosphate binder generally is amorphous, i.e., the binder material is essentially of amorphous character. Preferably less than about 10 mass-% of the binder pore volume is micropore volume, characteristic of crystalline material, and the micropore volume more preferably is less than 5% and optimally less than 2% of the pore volume. Crystalline aluminophosphate generally is unsuitable binder material for preparing a strong, crush-resistant catalyst. Material that is not in an amorphous phase generally is present as gamma-alumina; as the phosphorus content of amorphous aluminum phosphate is decreased, therefore, the proportion of crystalline material is increased. The average bulk density of the spheres also varies with the phosphorus content, as a higher proportion of phosphorus decreases the average bulk density. Surface area also is controlled by phosphorus content: gamma-alumina oil-dropped spherical particles typically have surface areas up to about 250 $m^2/g$, while spheroidal particles of aluminum phosphate may have surface areas of up to about 450 $m^2/g$. Al/P atomic ratios of the binder/matrix generally range from about 1/10 to 100/1, more typically from about 1/5 to 20/1, and often between about 1:1 and 5:1.

Best results are achieved when the catalyst has an X-ray diffraction pattern showing characteristic intensities of peaks at specified Bragg angle positions. Specifically, the preferred catalyst has an X-ray powder diffraction pattern such that the ratio of peak intensities at respective two-Θ Bragg angle positions of about 48.5:46.5 is at least about 1.1 and the ratio of peak intensities at respective two-Θ Bragg angle values of about 48.5:47.5 is at least about 1.0. The X-ray pattern may be obtained by standard X-ray powder diffraction techniques, of which a suitable example is described hereinbelow. Typically, the radiation source is a high-intensity, copper-target, X-ray tube operated at 45 KV and 35 mA. Flat compressed powder samples illustratively are scanned in a continuous mode with a step size of 0.030° and a dwell time of 9.0 seconds on a computer-controller diffractometer. The diffraction pattern from the copper K radiation may be recorded with a Peltier effect cooled solid-state detector. The data suitably are stored in digital format in the controlling computer. The peak heights and peak positions are read from the computer plot as a function of two times theta (two-Θ)), where theta is the Bragg angle.

It is within the scope of the invention that the catalyst contains a metal component, preferably selected from components of the group consisting of gallium, rhenium and bismuth. Preferably, however, the catalyst consists essentially of a zeolitic aluminosilicate having a pore diameter of from about 5 to 8 Å and an aluminum phosphate binder.

Optionally, the catalyst may be subjected to precoking in order to increase the proportion of paraxylene in the $C_8$ aromatics product. Precoking of the present catalyst effects a proportion of paraxylene in the product above equilibrium levels at disproportionation conditions, preferably at least about 80 mass-% and optimally about 90 mass-% or more of the $C_8$ aromatics. Precoking is effected on fresh or regenerated catalyst prior to its use for disproportionation at precoking conditions comprising usually at one or more of a higher temperature, lower space velocity, and lower hydrogen-to-hydrocarbon ratio relative to the disproportionation conditions. Such operating conditions generally are within the ranges of those disclosed before for disproportionation, with operating temperature generally being higher, and preferably being at least about 50° C. higher than the disproportionation temperature. Precoking time ranges from about 0.5 hours to 10 days. Precoking effects a catalyst carbon content of between about 5 and 40 mass-% carbon, and preferably between about 10 and 30 mass-% carbon. A coke-forming feed for precoking may comprise the feedstock as described herein, or other specific hydrocarbons or mixtures preferably comprising aromatics may be used. Further details relative to precoking are disclosed in U.S. Pat. No. 4,097,543, incorporated herein by reference.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

An aluminum-phosphate-bound MFI Catalyst A of the invention was prepared according to the following procedure. A first solution was prepared by adding phosphoric acid to an aqueous solution of hexamethylenetetraamine (HMT) in an amount to yield a aluminum:phosphorus atomic ratio in the binder of about 4:1. A second solution was prepared by adding an ammonia-exchanged MFI-type zeolite having an $Si/Al_2$ ratio of about 39 to enough alumina sol, prepared by digesting metallic aluminum in hydrochloric acid, to yield a zeolite content in the finished catalyst equal to about 77 mass-%. These two solutions were commingled to achieve a homogeneous admixture of HMT, phosphorus, alumina sol, and zeolite. This admixture was dispersed as droplets into an oil bath. maintained at about 93° C. The droplets remained in the oil bath until they set and formed hydrogel spheres having a diameter of about 1.6 mm. The spheres were removed from the oil bath, water washed, air dried, and calcined at a temperature of about 650° C. This disproportionation catalyst of the invention was designated Catalyst A.

Example II

Aluminum-phosphate-bound MFI catalysts not of the invention were prepared according to the procedure described in Example I with variations in the ratio of phosphorus to aluminum in the binder as indicated. A first solution was prepared by adding phosphoric acid to an aqueous solution of hexamethylenetetraamine (HMT) in an disproportionation amount to yield a alumina:phosphorus atomic ratio in the binder as shown below. A second solution was prepared by adding an ammonia-exchanged MFI-type zeolite having an $Si/Al_2$ ratio of about 39 to enough alumina sol, prepared by digesting metallic aluminum in hydrochloric acid, to yield a zeolite content in the finished catalysts as shown below. These two solutions were commingled to achieve a homogeneous admixture of HMT, phosphorus, alumina sol, and zeolite which was dispersed as droplets into an oil bath maintained at about 93° C. The droplets remained in the oil bath until they set and formed hydrogel spheres which were removed from the oil bath, water washed, air dried, and calcined at a temperature of about 650° C. The catalysts were designated and had composition characteristics as follows:

|  | Al/P Molar Ratio | MFI, Mass-% |
| --- | --- | --- |
| Catalyst B | 1 | 80 |
| Catalyst C | 2 | 77 |
| Catalyst D | 10 | 70 |

Example III

An alumina-bound MFI catalyst was prepared as a reference for contrasting characteristics and results with the disproportionation catalyst and process of the invention. Hexamethylenetetraamine (HMT) was added to a solution prepared by adding an ammonia-exchanged MFI-type zeolite having an $Si/Al_2$ ratio of about 39 to enough alumina sol, effected by digesting metallic aluminum in hydrochloric acid, to yield a zeolite content in the finished catalyst equal to about 70 mass-%. The components were commingled to achieve a homogeneous admixture of HMT, alumina sol, and zeolite. This admixture was dispersed as droplets into an oil bath maintained at about 93° C., wherein they remained until they set and formed hydrogel spheres having a diameter of about 1.6 mm. The spheres were removed from the oil bath, water washed, air dried, and calcined at a temperature of about 650° C. This reference catalyst was designated as Catalyst X.

Example IV

The X-ray powder diffraction pattern of Catalysts A, B, C, D, and X were obtained by standard X-ray powder techniques. The radiation source was a high-intensity, copper-target, X-ray tube operated at 45 KV and 35 mA. Flat compressed powder samples were scanned in a continuous mode with a step size of 0.030° and a dwell time of 9.0 seconds on a computer-controller diffractometer. The diffraction pattern from the copper K radiation were recorded with a Peltier effect cooled solid-state detector. The data were stored in digital format in the controlling computer. The peak heights and peak positions were read from the computer plot as a function of two times theta (two-Θ), where theta is the Bragg angle, and are shown for Catalyst A in FIG. 1. The ratio of peak intensities at respective two-Θ Bragg angle positions of about 48.5:46.5 and the ratio of peak intensities at respective two-Θ Bragg angle values of about 48.5:47.5 were determined for each catalyst as follows:

|  | Intensity Ratio | |
| --- | --- | --- |
|  | 48.5:46.5 2-Θ | 48.5:47.5 2-Θ |
| Catalyst A | 1.190 | 1.069 |
| Catalyst B | 1.077 | 0.966 |
| Catalyst C | 1.083 | 0.945 |
| Catalyst D | 1.034 | 0.968 |
| Catalyst X | 0.710 | 0.917 |

Example V

Pilot-plant tests were carried out to determine the comparative performance of the catalysts described hereinabove in a disproportionation reaction. The catalysts first were precoked at conditions comprising a temperature of about 560° C. and 4 weight hourly space velocity (WHSV) in the presence of a 1:5 hydrogen:nitrogen molar ratio for a period of time sufficient to effect approximately 90 mole-% paraxylene in total xylenes. Disproportionation of pure toluene then was carried out at 2.45 Mpa and 4 WHSV in the presence of pure hydrogen at varying temperatures as required to achieve 30% conversion of toluene. Results then were normalized based on pilot-plant correlations to provide a comparative molar ratio of benzene to xylenes in the product at 30% conversion and 90% paraxylene/xylenes.

Catalyst A was precoked over a period of 61 hours to provide a carbon content sufficient to control activity and selectivity as described hereinabove. Disproportionation of pure toluene then was effected at varying temperatures of 460° and 445° C.

Catalyst B was precoked over a period of 90 hours to provide a carbon content sufficient to control activity and selectivity as described hereinabove. Disproportionation of pure toluene then was effected at varying temperatures of 461° and 451° C.

Catalyst C was precoked over a period of 55 hours to provide a carbon content sufficient to control activity and selectivity as described hereinabove. Disproportionation of pure toluene then was effected at varying temperatures of 454° and 441° C.

Catalyst D was precoked over a period of 42 hours to provide a carbon content sufficient to control activity and selectivity as described hereinabove. Disproportionation of pure toluene then was effected at varying temperatures of 460° and 448° C.

Catalyst X was precoked over a period of 34 hours to provide a carbon content sufficient to control activity and selectivity as described hereinabove. Disproportionation of pure toluene then was effected at varying temperatures of 457°, 440° and 431° C.

The resulting benzene/xylene ratios at 30% conversion and 90% paraxylene/xylenes were as follows:

| | |
|---|---|
| Catalyst A | 1.45 |
| Catalyst B | 1.57 |
| Catalyst C | 1.58 |
| Catalyst D | 1.74 |
| Catalyst X | 1.73 |

Catalyst A of the invention clearly featured the most favorable ratio of benzene to xylenes.

We claim:

1. An oil-dropped spherical catalyst comprising a zeolitic aluminosilicate having a pore diameter of from about 5 to 8 Å and an aluminum phosphate binder, the catalyst having an X-ray powder diffraction pattern such that the ratio of peak intensities at respective two-Θ Bragg angle values of 48.5:46.5 is at least about 1.1.

2. The catalyst of claim 1 wherein the zeolitic aluminosilicate comprises a pentasil zeolite selected from the group consisting of MFI, MEL, MTW and TON.

3. The catalyst of claim 2 wherein the zeolitic aluminosilicate comprises MFI zeolite.

4. The catalyst of claim 3 wherein the zeolite has an enhanced surface silicon content.

5. The catalyst of claim 1 wherein the catalyst consists essentially of a zeolitic aluminosilicate having a pore diameter of from about 5 to 8 Å and an aluminum phosphate binder.

6. An oil-dropped spherical catalyst comprising a zeolitic aluminosilicate having a pore diameter of from about 5 to 8 Å and an aluminum phosphate binder, the catalyst having an X-ray powder diffraction pattern such that the ratio of peak intensities at respective two-Θ Bragg angle values of 48.5:46.5 is at least about 1.1 and the ratio of peak intensities at respective two-Θ Bragg angle values of 48.5:47.5 is at least about 1.0.

7. The catalyst of claim 6 wherein the zeolite has an enhanced surface silicon content.

8. The catalyst of claim 6 wherein the catalyst consists essentially of a zeolitic aluminosilicate having a pore diameter of from about 5 to 8 Å and an aluminum phosphate binder.

9. An oil-dropped spherical catalyst comprising a zeolitic aluminosilicate having a pore diameter of from about 5 to 8 Å and an aluminum phosphate binder, the catalyst having an X-ray powder diffraction pattern such that the ratio of peak intensities at respective two-Θ Bragg angle values of 48.5:46.5 is at least about 1.1, and further comprising an amount of between about 5 and 40 mass-% carbon as a proportion of the catalyst.

* * * * *